United States Patent [19]

Silander

[11] Patent Number: 4,477,574
[45] Date of Patent: Oct. 16, 1984

[54] METHOD OF TIME-MARKING SEDIMENTATION PROCESSES

[75] Inventor: Torsten G. Silander, Stockholm, Sweden

[73] Assignee: AB Tesi, Sweden

[21] Appl. No.: 406,228

[22] PCT Filed: Dec. 11, 1981

[86] PCT No.: PCT/SE81/00369
§ 371 Date: Aug. 2, 1982
§ 102(e) Date: Aug. 2, 1982

[87] PCT Pub. No.: WO82/02250
PCT Pub. Date: Jul. 8, 1982

[30] Foreign Application Priority Data

Dec. 23, 1980 [SE] Sweden .............................. 8009126

[51] Int. Cl.$^3$ .......................................... G01N 33/48
[52] U.S. Cl. ...................................... 436/70; 73/61.4; 210/800; 210/927
[58] Field of Search ................ 73/61.4; 210/516, 518, 210/927, 800, 789; 436/63, 70, 177, 178, 789

[56] References Cited

U.S. PATENT DOCUMENTS 3,647,070 3/1972 Adler ............................ 210/518 X
3,864,979 2/1975 Ayres ............................ 210/927 X
4,077,396 3/1978 Wardlaw et al. ............... 210/927 X
4,197,735 4/1980 Munzer et al. ...................... 422/103
4,257,886 3/1981 Kessler ........................... 210/927 X Primary Examiner—Arnold Turk
Attorney, Agent, or Firm—Silverman, Cass & Singer, Ltd.

[57] ABSTRACT

In a time-marking sedimentation process where two or more fractions in a sample containing liquid are to be separated entirely or partially by their specific weights in a tube or corresponding structure, a plug (2) of a hydrophilic plastic substance is brought into contact with the sample. The plug (2) has original dimensions smaller than the inner diameter of the tube (1) and has a specific weight lying between the specific weights of the fractions. The plug is adjusted with respect to its dimensions and/or substance so as to attain a swelling degree sufficient for the plug to jam in the tube (1), to mark the separation line between the fractions (3,4) after a certain predetermined period. Thereafter the position of the plug (2) in the tube is read. The method and device are particularly advantageous in medical connections, especially in the determination of the sedimentation reaction of blood, in which blood corpuscles are separated from plasma.

2 Claims, 4 Drawing Figures

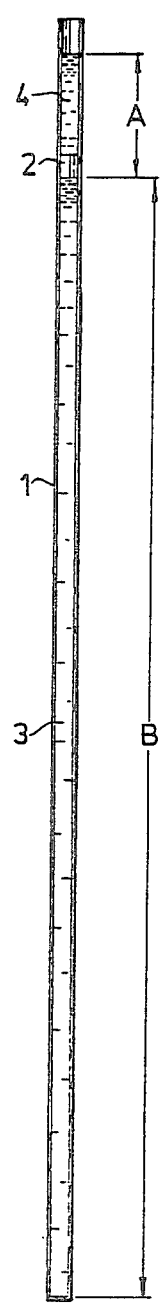
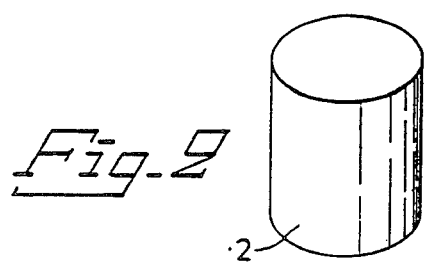
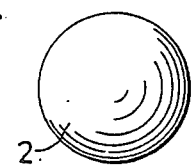
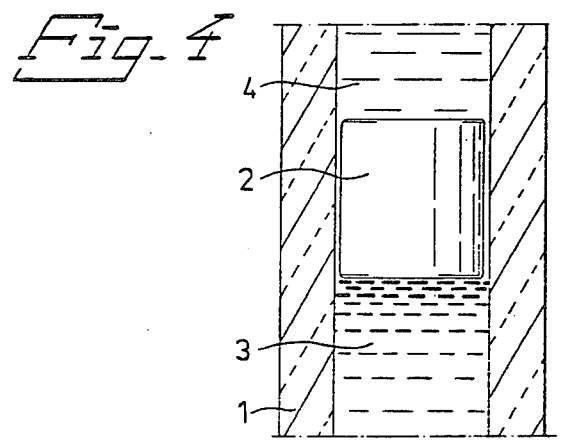
Fig. 1
Fig. 2
Fig. 3
Fig. 4

METHOD OF TIME-MARKING SEDIMENTATION PROCESSES

This invention relates to a method for time-marking sedimentation processes. The invention further relates to a device for carrying out the method.

Sedimentation processes in industry and medical service are, in this connection, to be understood as processes at which fractions with different densities are allowed to settle for a certain period in order thereby to be able to determine a relation between the different fractions with respect to, for example, the amount or differences in specific weight.

One example of a medical sedimentation process, for which the present invention is particularly well adapted, is the determination of the sedimentation reaction (SR) of the blood. In order to determine the sedimentation reaction, a blood sample with a small amount of sodium citrate solution added thereto is sucked or pressed up in a tube or hose having an inner diameter of 2.5 mm to a height of about 200 mm. The blood is allowed to settle for an accurate period of normally one hour.

Hereby blood corpuscles are collected in the lower portion of the tube, and a column of blood plasma above the blood corpuscles is clearly readable as regards the height of the plasma column.

Normal blood, so-called whole blood, has a specific weight of 1.06 g/cm$^3$. The blood corpuscles collected in the lower portion of the tube have a density of about 1.1 g/cm$^3$, while the plasma column has a density of about 1.02 g/cm$^3$.

The sedimentation process commences immediately after the taking of blood sample. The blood, therefore, must immediately be placed in the tube. The process continues until blood corpuscles and plasma substantially entirely have been separated.

According to standards, it has been determined to read the height of the plasma column after precisely one hour, in spite of the fact that the sedimentation process is not completed. In practice, therefore, a sedimentation sample cannot be utilized if the height of the plasma column is read at a time other than precisely after one hour.

In Sweden about 80,000 sedimentation reactions are determined every day. This implies a heavy work load for the staff because all of these reactions must be read after precisely one hour. The present invention solves this problem, because it is possible according to the invention to read the sedimentation reaction at any time after one hour has passed, for example after a period as long as one or several days.

The present invention, thus, relates to a method of time-marking sedimentatio processes, in which two or more fractions in a sample containing liquid are to be separated entirely or partially by their specific weights in a tube or the like.

The invention is characterized in that a plug of a hydrophilic substance, preferably a plastic substance, is brought into contact with the sample, which plug has a specific weight of between the specific weights of said fractions, and which plug with respect to its dimensions and/or substance is adjusted so as to attain a swelling degree sufficient for the plug to jam in the tube and to mark the separation line between the fractions after a certain, predetermined period, and that after said period the position of the plug in the vertical direction of the tube is read.

The invention further relates to a device for carrying out the method, which device is of the kind and has substantially the characterizing features as defined in the claims.

The invention is described in greater detail in the following, with reference to the accompanying drawing, in which FIG. 1 shows a sedimentation reaction tube on a scale of 1:1 where the invention is utilized, FIG. 2 shows an embodiment of a plug on an enlarged scale, which plug is associated with the invention, FIG. 3 shows a different embodiment of said plug on an enlarged scale, and FIG. 4 shows a section of a sedimentation reaction tube with a plug on an enlarged scale.

The method according to the invention proceeds so that blood is placed in a normal way in a sedimentation reaction tube. Either prior or subsequent to the placement of the blood, a plug consisting of a hydrophilic material is inserted in the tube. It is preferable, however, to insert the plug 2 into the tube prior to the liquid, so that the plug floats up through the blood. The plug has a specific weight lying between the specific weight of the blood corpuscles and the specific weight of the plasma.

The specific weight of the plug preferably is chosen to be below the specific weight of whole blood but above the specific weight of the plasma, in which case the plug floats on a column of whole blood, but sinks through the plasma.

A hydrophilic plastic material suitable for use at the present invention is a hydrophilic plastic substance, a so-called hydrogel, preferably vinylpyrrolidone. Also other hydrophilic plastic substances can be used, and the specific weight of the material, when necessary, can be adjusted so as to be increased or reduced. This adjusting can be effected in known manner, for example by admixing another material.

Hydrophilic plastic materials of the kind here referred to suck up liquid and thereby increase their volume. This implies, thus, that a plug of hydrophilic material with the aforesaid specific weight inserted into a tube floats above the blood corpuscle column 3, but sinks in the plasma column 4. The plug 2 further absorbs liquid in the tube 1, and after a certain time the plug 2 jams in the tube 1. In FIG. 1 a sedimentation reaction tube 1 as shown, into which a plug 2 according to the invention has been inserted and swelled therein. In FIG. 1 the blood introduced into the tube is assumed to have settled so that a column 3 of blood corpuscles has been formed below the plug 2, and so that a column 4 of plasma has been formed above the plug 2. The sedimentation reaction is read as the distance A, which corresponds to the height of the plasma column 4, or as 200 mm minus the distance B, which distance is equal to the height of the blood corpuscle column when the distances A+B are equal to 200 mm.

The plastic material to be used according to the present invention has such a swelling degree per time unit that, in combination with the original size of the plug, the plug jams after one hour counted from the time when the whole blood and the plug 2 were combined in the sedimentation reaction tube 1.

The original dimensions of the plug 2 are such, that its greatest measure is slightly smaller than the inner diameter of the sedimentation reaction tube. Depending on the plastic material being used, the greatest measure is about 70% to 95% of the inner diameter of the sedimentation reaction tube.

It is obvious that the invention can be utilized in sedimentation processes other than medical ones. The invention can be utilized also in other medical sedimentation processes. It is, of course, necessary to adjust the original size of the plug 2 and the swelling degree per time unit of the plastic material in the liquid in question and also the specific weight of the plastic material to the time during which the sedimentation process is to proceed.

Manufacturers of hydrophilic plastic material, for example the company Special Polymers Ltd, England, can supply information on the swelling degree of the plastic materials and on other technical data desired.

As the plastic materials per se do not constitute a part of the present invention, they are here not described in greater detail.

In FIG. 2 a preferred embodiment of the plug 2 is shown. It is a cylinder with a diameter smaller than or equal to the height. A plug 2 of this configuration floats in a stable manner on the blood corpuscle column 3, as shown in FIG. 4. This increases the safety in the determination of the desired level, both with respect to easy reading and to a possible penetration of blood corpuscles upward above the lowermost surface of the plug 2. The plug 2 may also be a ball, whereby the advantage is gained that the geometric orientation of the plug 2 in the tube is of no importance.

The present invention, thus, renders it possible to read the sedimentation reaction practically at any time after one hour has passed since the sedimentation test was started. The advantages of the invention are fully apparent in consideration of the work load and deficient accuracy, which are unavoidable due to the fact that a conventional sedimentation reaction must be read after exactly one hour. The present invention, of course, requires modification of the plastic material in view of the sedimentation process to be examined.

It is further possible by the invention to mark the separation line between more than two fractions in a tube, by utilizing more plugs with a swelling degree and specific weight adjusted in a manner corresponding to that described above.

The hydrophilic substance preferably is a plastic substance, but may also be a cellulose substance, a textile or other hydrophilic substance. The invention, thus, must not be regarded restricted to the embodiment set forth above, but can be varied within the scope of the attached claims.

I claim:

1. A method of time-marking the end of a reaction period of certain length in a sedimentation process in which at least two fractions in a sample containing liquid are to be separated at least partially according to their specific weights in a tube by non-centrifugal sedimentation for a certain period, the method comprising:

contacting said sample in said tube, prior to sedimentation, with a plug of hydrophilic substance that has original dimensions smaller than the inner diameter of the tube and a specific weight lying between the specific weights of said fractions, and the plug having a swelling rate related to its dimensions and substance adjusted for the plug to absorb liquid during the sedimentation, and thereby to swell and jam in the tube after a predetermined period of time corresponding to said certain period, and mark the separation line between the fractions at the end of said certain period;

allowing said non-centrifugal sedimentation to occur; and reading the position of the plug in said tube in a vertical direction after said certain period.

2. The method of claim 1 in which said step of contacting includes inserting the plug into the tube prior to the liquid being inserted in the tube.

* * * * *